United States Patent
Rich

(10) Patent No.: US 9,782,183 B1
(45) Date of Patent: Oct. 10, 2017

(54) SURGICAL VIEWING SYSTEM

(71) Applicant: David B. Rich, Warsaw, IN (US)

(72) Inventor: David B. Rich, Warsaw, IN (US)

( * ) Notice: Subject to any disclaimer, the term of this patent is extended or adjusted under 35 U.S.C. 154(b) by 0 days.

(21) Appl. No.: 15/445,215

(22) Filed: Feb. 28, 2017

Related U.S. Application Data

(63) Continuation of application No. 15/441,759, filed on Feb. 24, 2017.

(51) Int. Cl.
    *A61B 17/17* (2006.01)
    *A61B 90/00* (2016.01)

(52) U.S. Cl.
    CPC .......... *A61B 17/1703* (2013.01); *A61B 90/37* (2016.02); *A61B 90/39* (2016.02); *A61B 2090/376* (2016.02); *A61B 2090/3966* (2016.02)

(58) Field of Classification Search
    CPC .............................. A61B 17/17; A61B 90/00
    See application file for complete search history.

(56) References Cited

U.S. PATENT DOCUMENTS

| | | | |
|---|---|---|---|
| 5,478,343 A | 12/1995 | Ritter | |
| 6,477,400 B1 | 11/2002 | Barrick | |
| 8,942,345 B2 | 1/2015 | Dennerlein et al. | |
| 2002/0193800 A1* | 12/2002 | Kienzle, III | A61B 17/1703 606/80 |
| 2004/0167391 A1* | 8/2004 | Solar | A61B 34/20 600/411 |
| 2009/0054910 A1* | 2/2009 | Zheng | A61B 17/1703 606/130 |
| 2010/0241129 A1* | 9/2010 | Markey | A61B 17/1626 606/104 |
| 2012/0022544 A1 | 1/2012 | Chang et al. | |
| 2012/0059376 A1 | 3/2012 | Rains et al. | |
| 2014/0107471 A1 | 4/2014 | Haider et al. | |
| 2014/0148808 A1 | 5/2014 | Inkpen et al. | |

\* cited by examiner

*Primary Examiner* — Christopher Beccia
(74) *Attorney, Agent, or Firm* — Taylor IP, P.C.

(57) ABSTRACT

A surgical viewing system including an X-ray source, a screw placing surgical tool, a detector, a fiducial marker, and an image correction system. The X-ray source creates a beam of radiation, and the surgical tool is coupled thereto. The X-ray detector detects an image, the detected image resulting from receiving a portion of the radiation. There is at least one fiducial marker coupled to a part of the surgical tool, the fiducial marker being radiopaque and blocking a portion of the beam of radiation from the detector to produce a profile on the detected image. The surgical tool has an axis of rotation and the fiducial marker is axially symmetric to the axis of rotation. The image correction system takes the detected image and produces a corrected image by using a shape of the profile of the fiducial marker and/or a location of the profile of the fiducial marker.

20 Claims, 17 Drawing Sheets

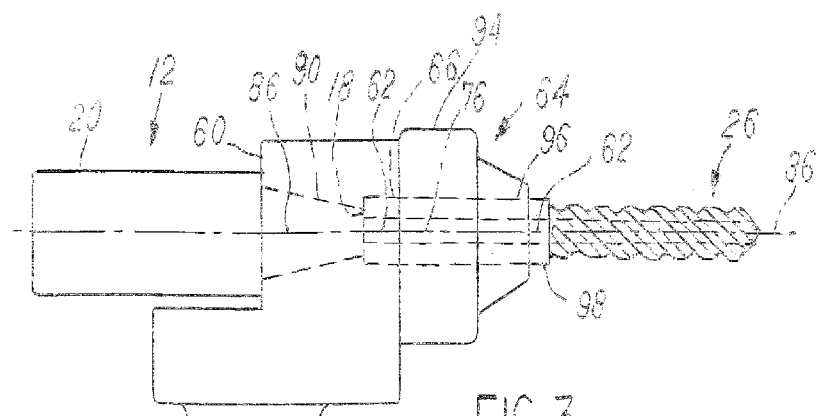
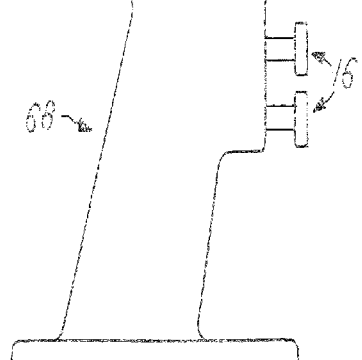
FIG. 3
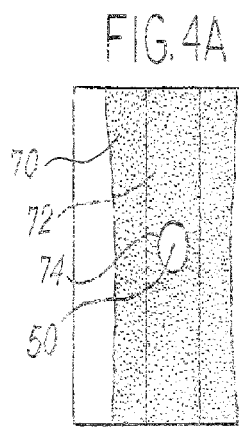
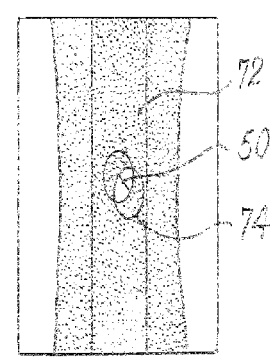
FIG. 4A   FIG. 4B

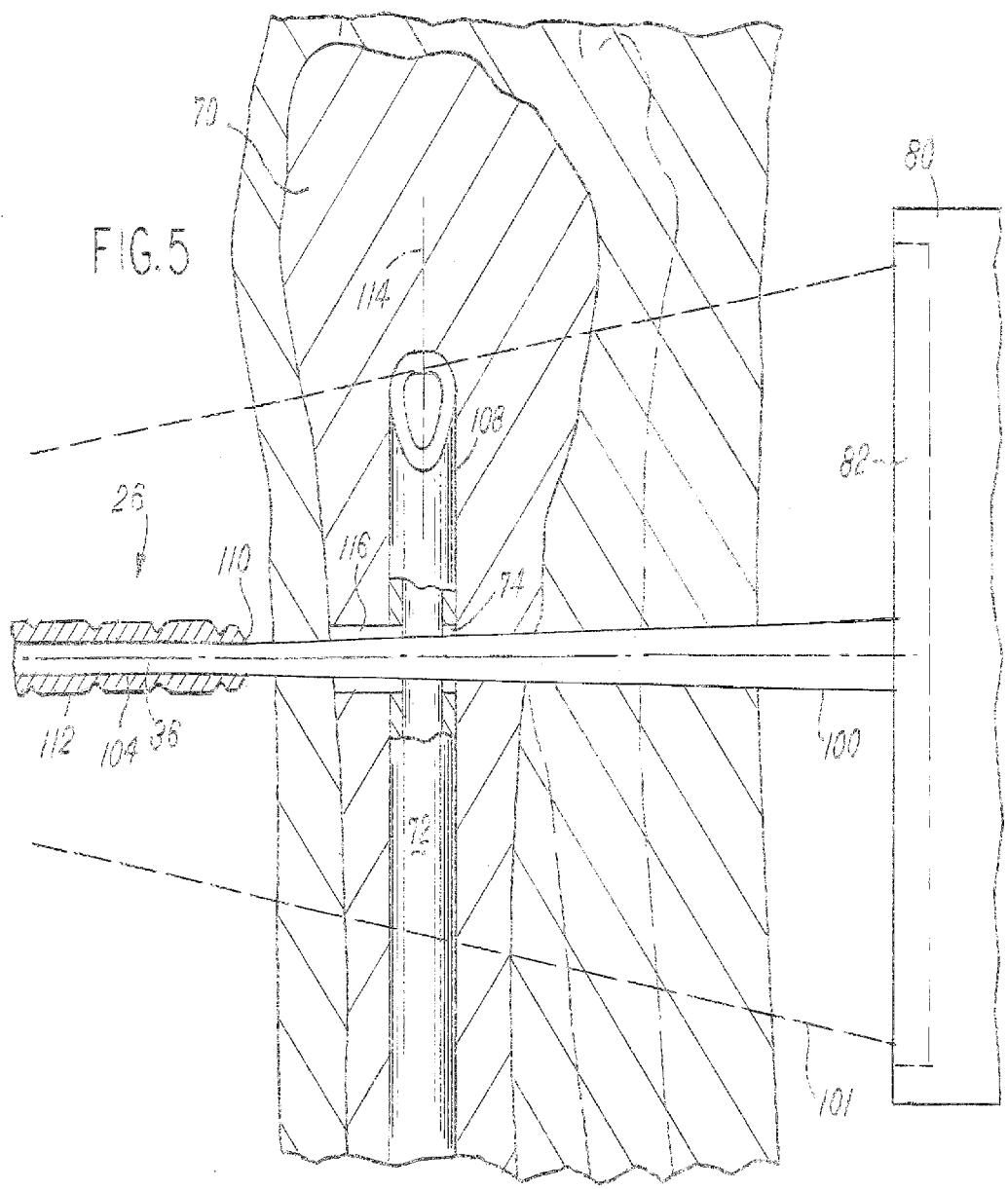

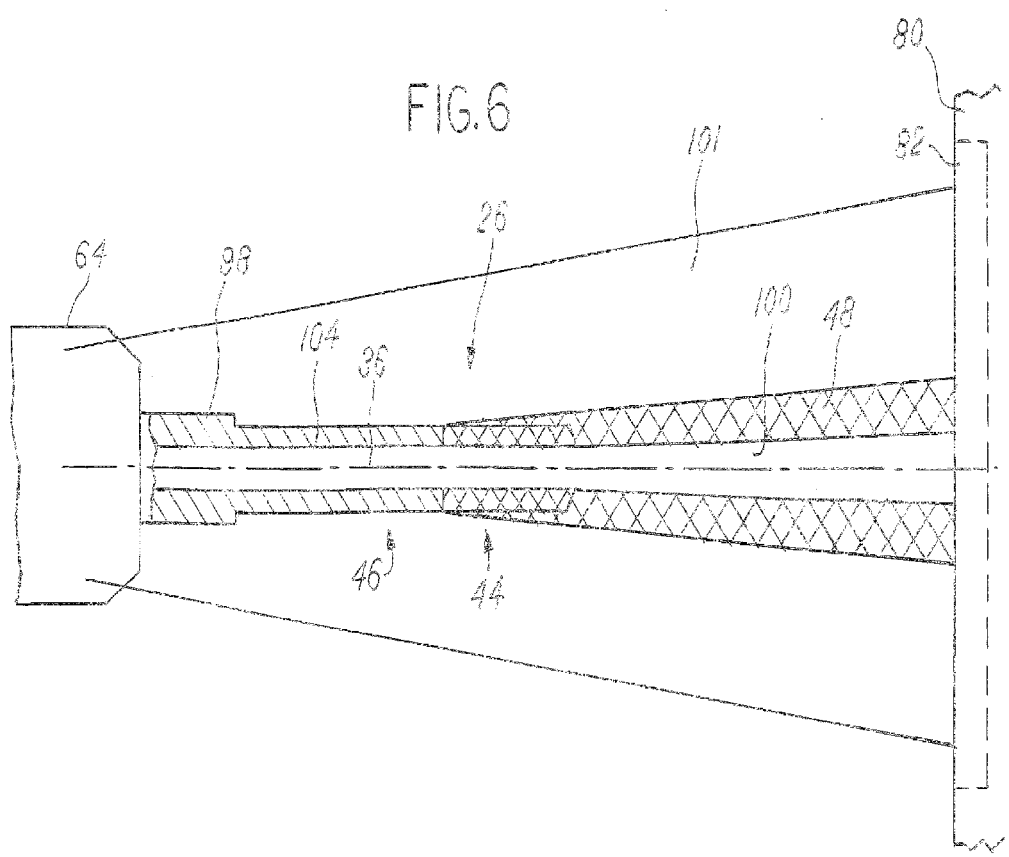

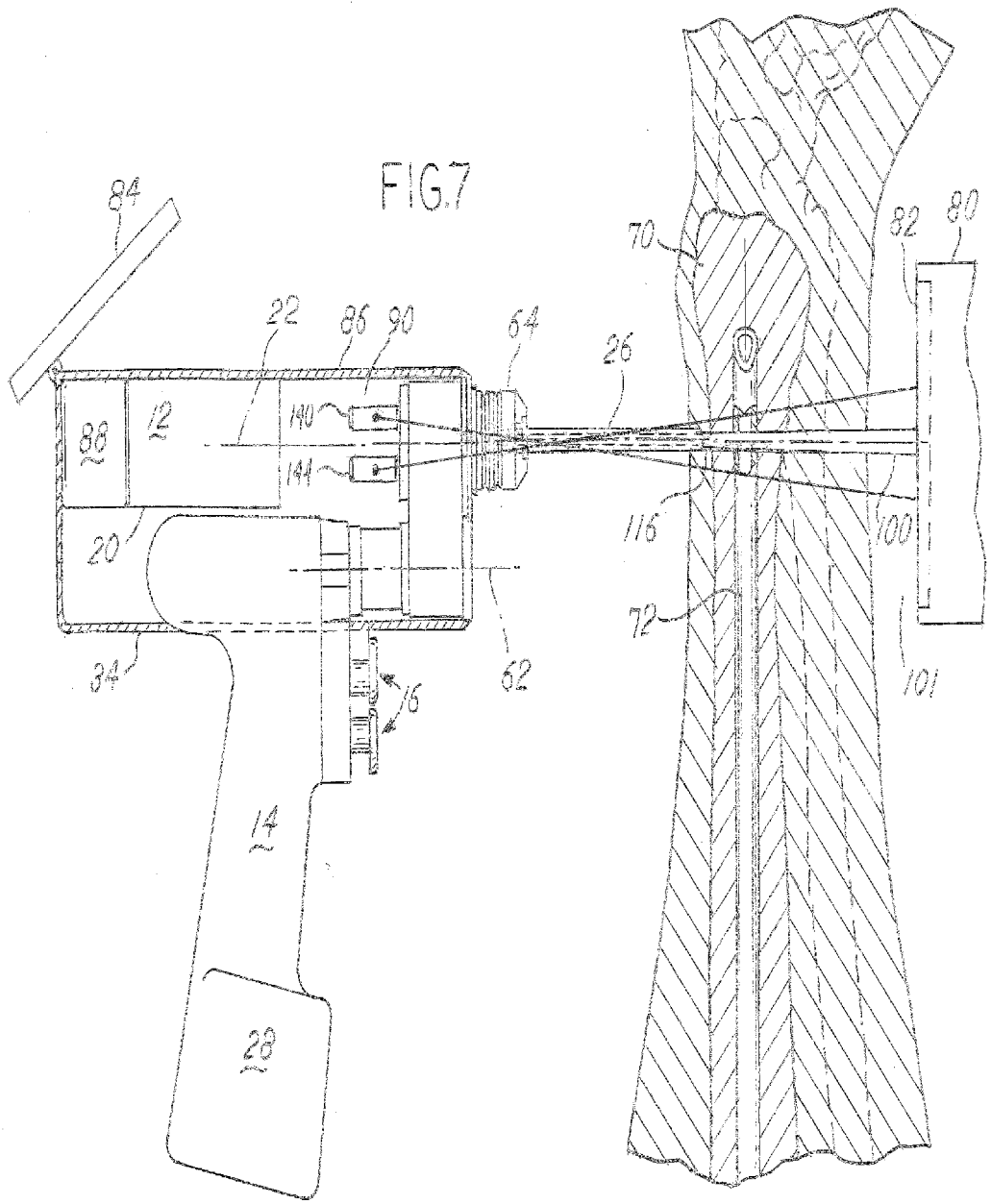

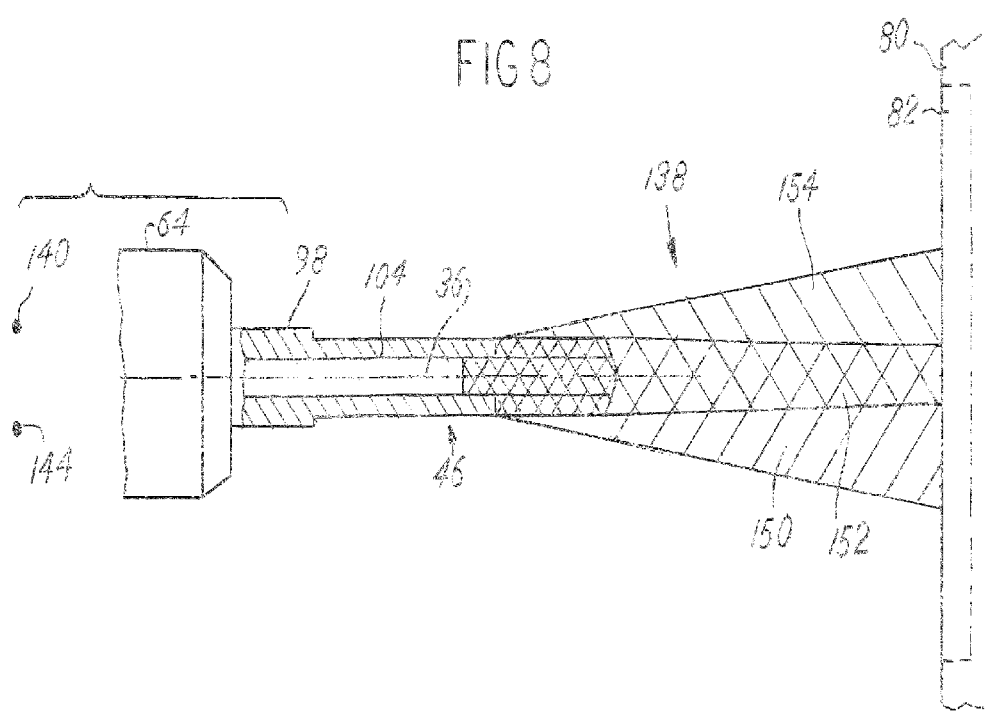

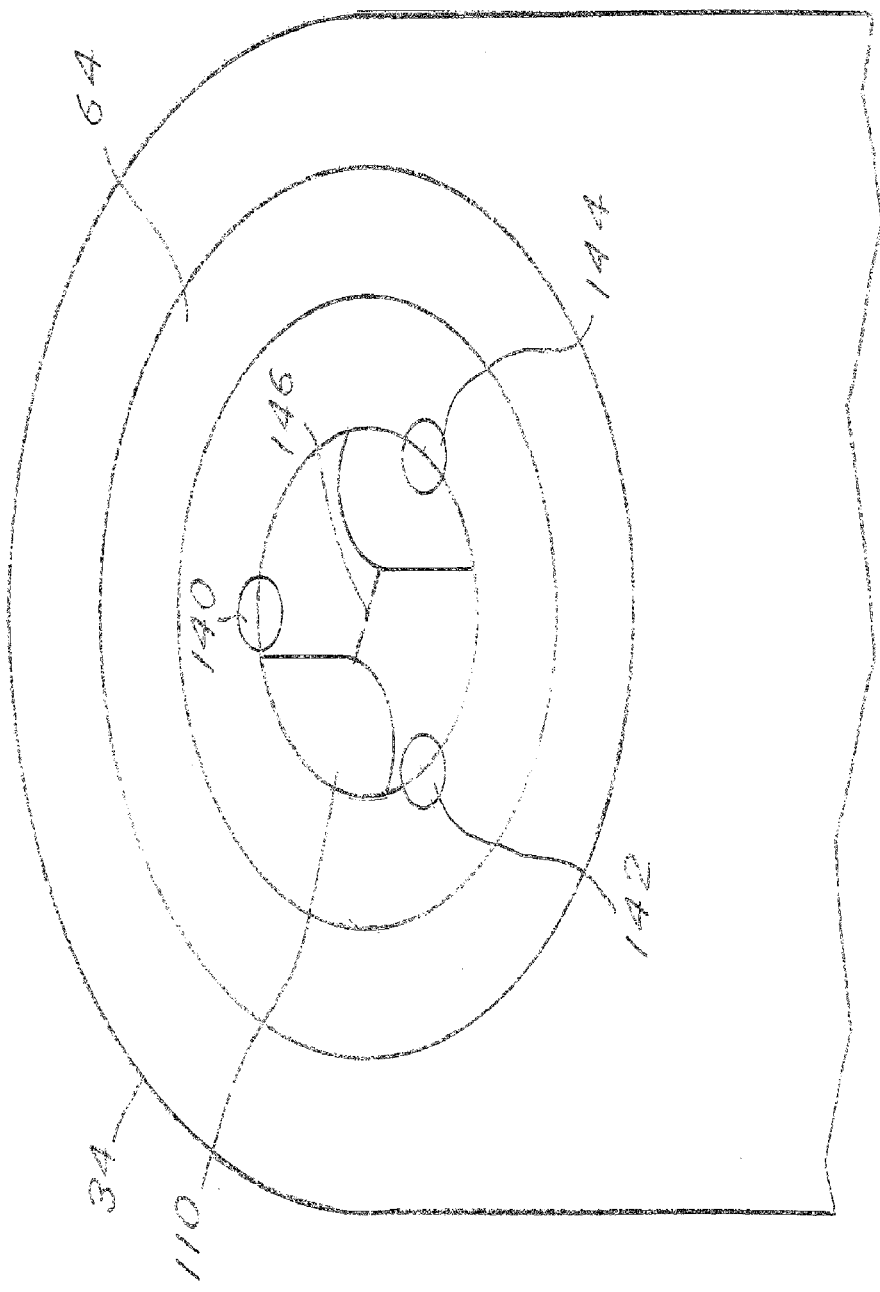

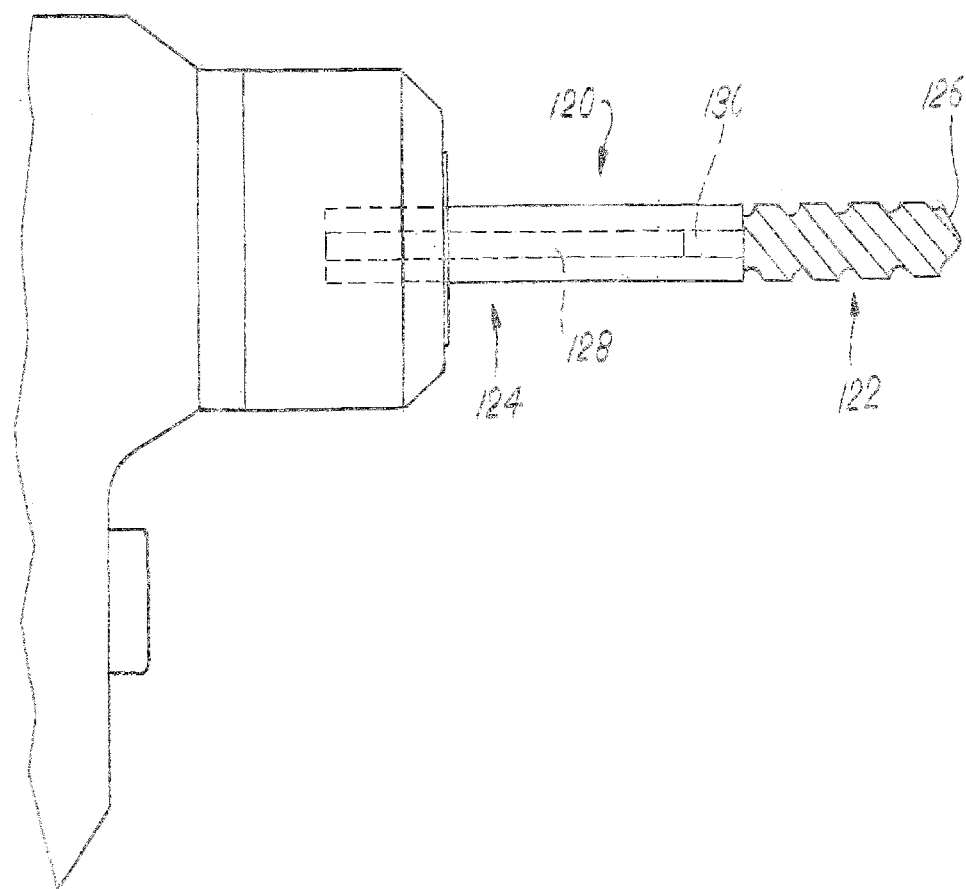

SURGICAL VIEWING SYSTEM

CROSS REFERENCE TO RELATED APPLICATIONS

This is a continuation of U.S. patent application Ser. No. 15/441,759, entitled "SURGICAL VIEWING SYSTEM", filed, Feb. 24, 2017, which is incorporated herein by reference.

BACKGROUND OF THE INVENTION

1. Field of the Invention

The present invention relates to a surgical viewing system, and, more particularly, to a surgical viewing system coupled to a screw placing surgical tool.

2. Description of the Related Art

Currently there are methods and devices that are used to assist the professional during the installation of an intramedullary nail. An intramedullary nail is designed to be inserted through the center of a bone and affixed to the bone via screws that are installed through the bone. The nail has pre-existing holes along its length, but when the nail is inserted to a bone, the holes are no longer visible. One option uses a fluoroscope to sight the hole, then the user places the drill based on the image seen on a monitor. The fluoroscope is then moved out of the way, the drill is then rotated into position and drilling is started. This involves a significant amount of practice and skill, since there is no visual feedback after the fluoroscope is moved and drilling starts. One option uses magnetics to sense the holes in the nail. Another option involves a drilling template that is affixed to one end (the proximal end) of the nail. This is ineffective, since the template can become easily misaligned and the nail sometimes bends upon insertion to the bone, rendering the template useless. A bent nail or misaligned template results in an incorrectly drilled hole. An incorrectly drilled hole results in longer surgery, higher potential for infection, and other trauma that can cause post-op complications.

Surgeons can also use pedicle probes to open up a path for screw placement, with an awl or high-speed burr being used to cut through dense cortical shell of vertebrae before using the probe.

The viewing of the alignment of the drill and screw can be misaligned if the transmitter and receiver are not aligned with each other.

What is needed in the art is an easy to operate surgical viewing system that uses a detector that is not necessarily perfectly aligned with an X-ray source.

SUMMARY OF THE INVENTION

The present invention provides a system that interprets a misalignment of the detector and compensates the image for the misalignment.

The invention in one form is directed to a surgical viewing system including an X-ray source, a screw placing surgical tool, a detector, a fiducial marker, and an image correction system. The X-ray source creates a beam of radiation, and the screw placing surgical tool is coupled thereto. The X-ray detector detects a projected image resulting in a detected image, the detected image resulting from receiving at least some of the beam of radiation. There is at least one fiducial marker coupled to a part of the screw placing surgical tool, the fiducial marker being radiopaque and blocking a portion of the beam of radiation from the detector to produce a profile on the detected image. The screw placing surgical tool has an axis of rotation and the fiducial marker is axially symmetrical to this axis of rotation. The image correction system takes the detected image and produces a corrected image by using a shape of the profile of the fiducial marker and/or a location of the profile of the fiducial marker.

The invention in yet another form is directed to a method of viewing a surgical item in an animal, the method including the steps of creating a beam, coupling a screw placing surgical tool, detecting a projected image, coupling a fiducial marker, and correcting an image. The creating a beam step creates a beam of radiation from an X-ray source. The coupling a screw placing surgical tool step couples a screw placing surgical tool with the X-ray source. The detecting a projected image detects a projected image with an X-ray detector resulting in a detected image, the detected image resulting from receiving at least some of the beam of radiation by the detector. The coupling at least one fiducial marker step couples the fiducial marker to a part of the screw placing surgical tool, the at least one fiducial marker being radiopaque and blocking a portion of the beam of radiation from reaching the detector to produce a profile on the detected image. The screw placing surgical tool has an axis of rotation and the fiducial marker is axially symmetrical to this axis of rotation. The correcting step corrects the detected image and produces a corrected image with an image correction system using at least one of a shape of the profile of the fiducial marker and a location of the profile of the fiducial marker.

An advantage of the present invention is that the fiducial maker is associated with the tool and projects a profile on the detector to allow the correction system to skew the image data to a true image for the surgeon.

Another advantage of the present invention is that the detector does not have to be aligned as in prior art systems.

Yet another advantage of the present invention is that there is no need to use a positioning system to either align the detector or to detect the orientation of the detector.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 3 is a side view of the system using a cannulated drill;

FIG. 4a is a side view of the display with the hole properly aligned;

FIG. 4b is a side view of the display with the hole misaligned;

FIG. 5 is a partial view of the drill bit and bone in FIG. 1;

FIG. 6 is a section view of a drill bit showing an occluded area;

FIG. 7 is a side view of a multi-point source embodiment;

FIG. 8 is a section view of the occluded area from the embodiment in FIG. 7;

FIG. 9 is a front view of a multiple source embodiment;

FIG. 10 is a side view of an alternate drill bit embodiment.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
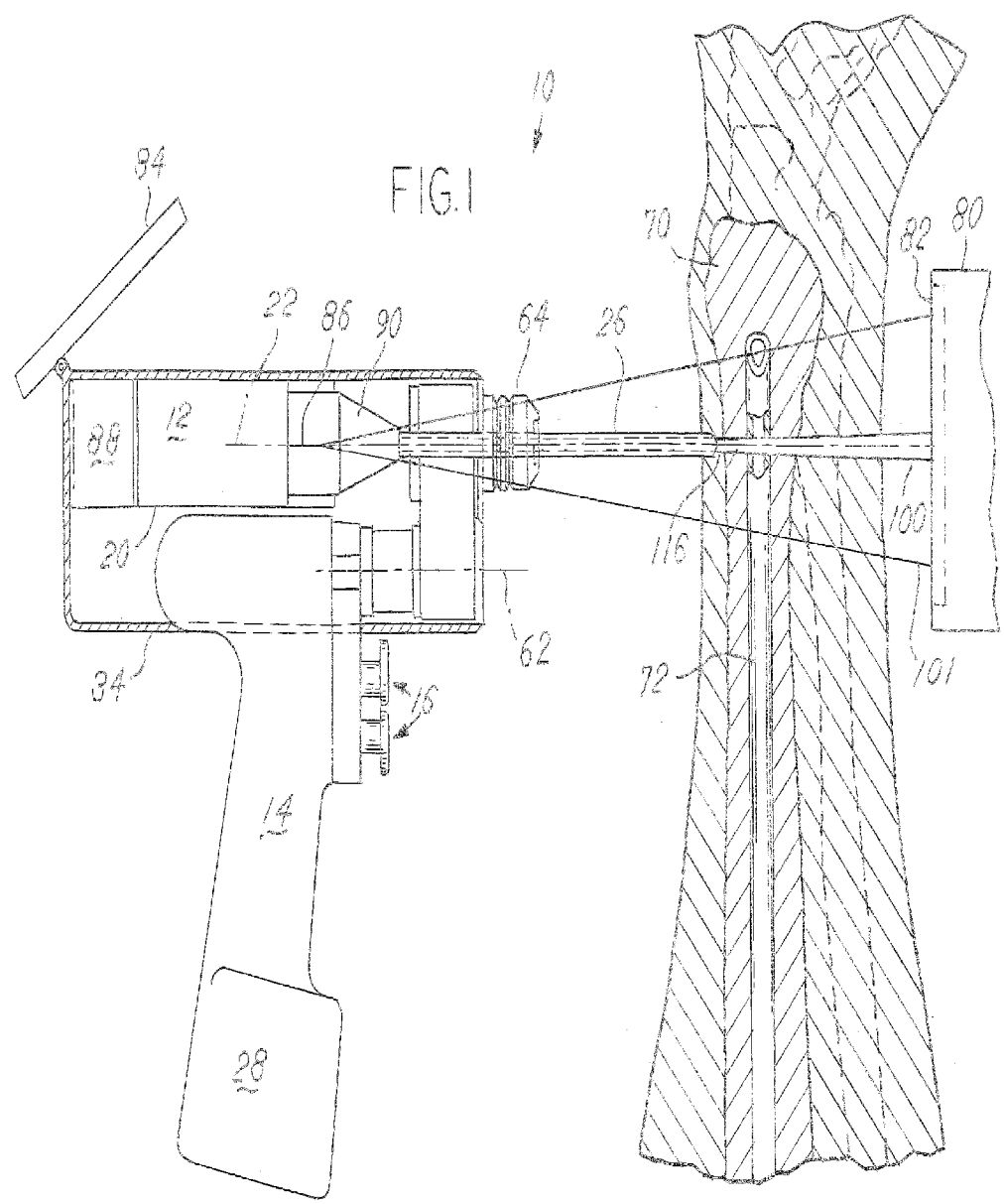
FIG. 1 is a side view of the system.
Figure 2:
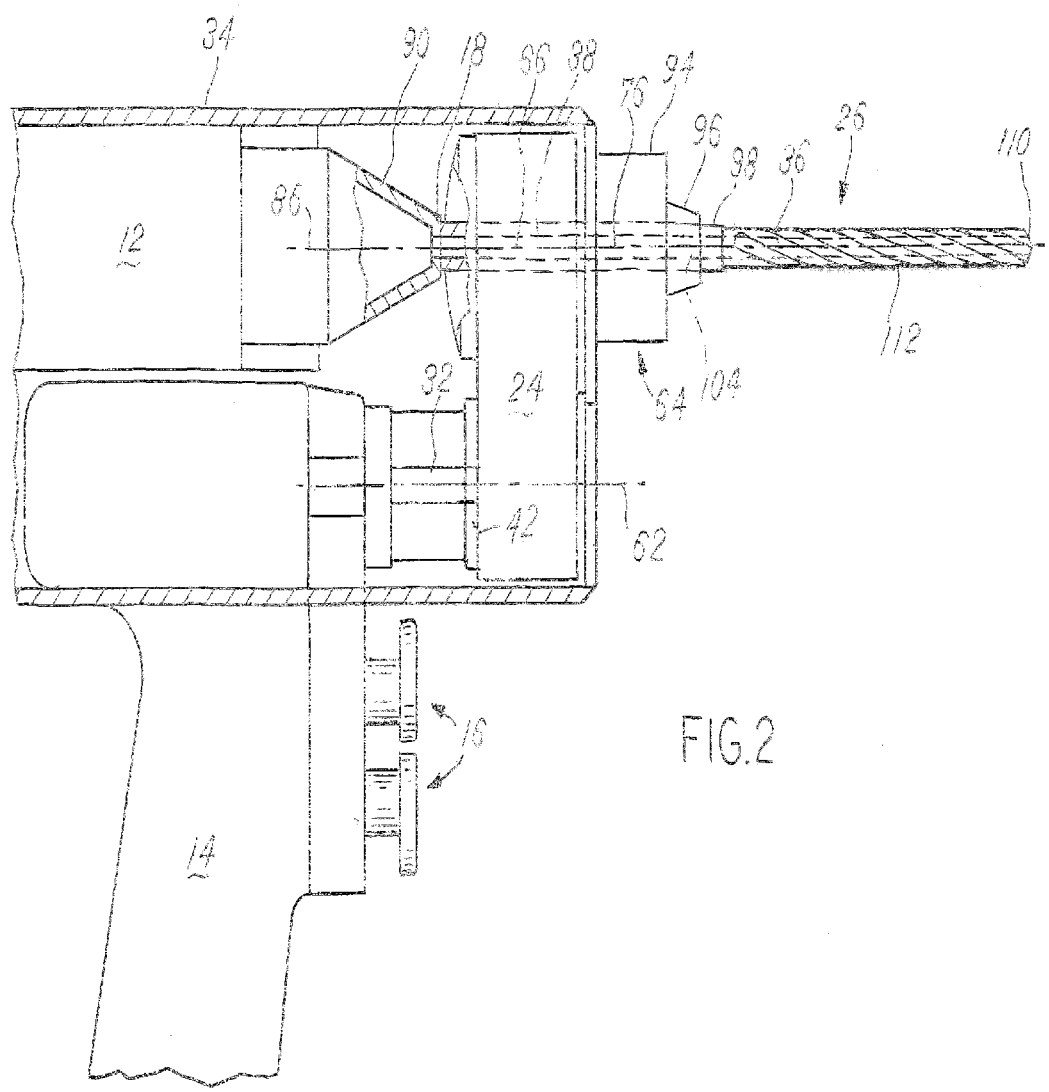
FIG. 2 is a partial view of the drill in FIG. 1.

The system 10 uses an X-ray source 12 and imager 80, a drill driver 14 as shown in FIG. 1, a cannulated drill 68 as shown in FIG. 3, a collimator 90 as shown in FIG. 2, and a cannulated drill bit 26. The purpose of the system is to guide the user for drilling a hole in a visually opaque medium (such as a bone 70) but is at least partially transparent to x-ray radiation 100. Radiodensity, radiolucency, and radiopacity are all terms that describe the degree to which a material or device blocks x-ray radiation. Radiolucency is on the more transparent side of the scale, radiopaque materials being the least transparent. Radiodense materials have properties that attenuate x-ray radiation. For the purposes of this specification, "radiation" describes x-ray radiation and "radiograph" is a representation of radiation as it is received by a medium or device and displayed such that it can be viewed by the user. The primary focus of this specification and the embodiments described involve an intramedullary nail, but the system can be used for plates or other devices that lack a useful visual alignment method. For the system to be effective, the bone, nail or other features need to show up as contrasting parts of an image on a radiograph.

In orthopedics, a broken or damaged bone 70 can be reinforced with an intramedullary nail 72 inserted through one end of the bone. Intramedullary nails have been used in the medical field for years and are well known in the art. The nail 72 can be either curved or straight but is typically round on the outside. The nail 72 is an elongate member with a proximal end and a distal end 108 as shown in FIG. 5. The nail 72 has transverse holes 74 as shown in FIG. 5 through the center 114 along the length that are angled to the center 114. The nail 72 is made from a biocompatible material, such as titanium and can be hollow, solid, or have portions that involve a combination of the two. The nail 72 as shown in FIGS. 1 and 5 is a hollow tube. In order to secure the nail 72 to the bone 70, locking screws are driven through the bone and the transverse hole 74. In order to drive the locking screw and secure the nail, a hole must first be drilled through the bone. The drilled hole 116 must line up with the axis of the transverse hole 74 for the locking screw to be properly driven into the bone 70 and nail 72. The center 114 of the outer diameter is created along the length between the proximal and distal 108 ends. The distal end 108 is inserted first and extends into a blind hole in the bone 70. The proximal end is the last portion to be inserted. After the nail 72 is completely inserted and positioned in the bone 70, a hole 116 is drilled through the side of the bone as shown in FIG. 5. For proper installation of a locking screw (not shown), the drilled hole 116 must be coaxial to the transverse hole 74 in the nail 72. The locking screw can be driven through both the drilled hole 116 and the transverse hole 74 in the nail 72. The screw anchors the bone 70 to the nail 72, thereby reinforcing or aligning it.

When a source of x-ray radiation is coupled with a device to receive and display the radiation (such as a radiograph), the user can see things that are internal to the visually opaque material. This is useful because fractures and breaks in bones are not always detectable otherwise. An x-ray source 12 is made up of a housing 20 as shown in FIGS. 1 and 3 with an aperture 18 and a generator 22 as shown in FIG. 1. The x-ray source 12 includes a power supply 88 that is integral as shown in FIG. 1 or could be external. The power supply 88 is typically a battery. A majority of the housing 20 is radiopaque, meaning it is made from materials that x-ray radiation does not penetrate through, thereby directing it only through the aperture 18 as shown in FIG. 2. Radiopaque materials (such as lead) are used to block stray radiation that would irradiate surrounding areas. The generator 22 generates x-ray radiation as a point source inside of the housing 20 and typically includes a collimator 90 to direct the radiation. The collimator 90 is designed to selectively pass a narrow beam of radiation 101 from the generator 22 along an axis 86 that exits through the aperture 18, and blocks all other rays. The aperture 18 is made from radiolucent materials, meaning that x-ray radiation can pass through. As shown in FIG. 1, the radiation 101 expands outward to a certain extent after leaving the collimator 90. X-ray sources 12 with collimated radiation 101 are commonly known in the art. The x-ray source 12 can be operated continuously for a live feed of radiation or be triggered by the user to generate single snapshots. The x-ray source 12 can be made of separate components but is shown as an integrated assembly. In the separate component construction, the generator 22 is connected to the power supply 88 via high voltage cable. As shown in FIG. 1, the collimator 90 creates a central axis 86 for the x-ray radiation 100, 101.

An imager 80 is made up of a panel 82 and a display 84 as shown in FIGS. 1 and 7. The panel 82 is used to receive the x-ray radiation and convert it to a radiograph image that can be viewed by the user on a display 84. X-rays penetrate various density materials in various amounts. Materials that inhibit the transmission of x-ray radiation have radiodense properties. Any physical matter with radiodense properties in the path of radiation 100, 101 (as it is projected onto the panel 82) shows up as a shadow, the intensity of the shadow is proportional to the radiodensity of the item. The different densities are visible in FIGS. 4a and 4b. For example, a lower density material (like muscle, cartilage, or other soft tissue) attenuates the radiation to a lesser extent than a more dense material. Different metals have different radiodensities and show up differently on a radiograph. The panel 82 is attached to a display 84. The display 84 can be remotely located or integrated in any part of the device 10. The display 84, as shown in FIG. 1, is mounted on the rear of the drill housing 34, source housing 20, or cannulated drill 14. Lower density materials are shown as contrasting areas as compared to more dense materials, making it possible for the user to distinguish between the two. The display 84 can be programmed to be triggered by snapshots of x-ray radiation or display a live video feed of the radiation as received by the panel 82. The snapshots limit the amount of radiation the patient receives and the live video feed gives the user a continuous feedback. Further, data processing and algorithms can be integrated into the display 84 or panel 82 such that features or conditions trigger supplemental information to be displayed. The data processing can be done in an intermediate part that is located in the path of communication between the panel 82 and the display 84. For example, transitions between a nail and a transverse hole can be highlighted with a distinct color. Fiducial markers 50 as shown in FIGS. 4A and 4B can be included with the data processing, where specific shapes could trigger highlighting, a superimposed bulls-eye, or color changes as alignment improves. Data processing and display of such data can be used as an additional tool to assist alignment by the user.

A cannulated drill 68 as shown in FIG. 3 supplies rotational torque along a driving axis 62. A cannulated drill 68 is similar to a common medical drill but has a passage 66 having a central axis 76 completely through the driving axis 62 of a cannulated chuck 64. As with any piece of medical equipment, a cannulated drill 68 is built from materials that can be sterilized and are suitable for medical use. Speed, direction, and torque are controlled by the user, typically through a control 16. As with a standard drill, the cannulated drill 68 consists of a power source (a battery pack 28 as shown in FIGS. 1 and 3), motor, gears, housing, and cannulated chuck 64. Optionally, the drill can be pneumatically driven or use a separate power source. The cannulated drill 68 is controllable remotely or locally. A cannulated chuck 64 is designed to interface or mate with an external shaft or device such as a drill bit 26. The cannulated chuck 64 is driven by the output of the gears and usually consists of a body cap 94 and jaws 96. The body cap 94 closes or opens the jaws 96 of the chuck 64 to respectively tighten or loosen around the shank 98 of a drill or another driven shaft. The body cap 94 can be tightened by hand or with a key as is commonly known in the art. While a standard medical drill driver 14 has a chuck that lacks a passage, a cannulated drill 68 has a passage 66 through the axis of the drill 62 as shown in FIG. 3. The rear of the drill is a mounting 60 and a receiving portion 30 that is used to mount the x-ray source 12. The housing 20, collimator 90 as shown in FIG. 2, or aperture 18 can be places the source 12 can mount to the drill 68. The mounting 60, inline with the chuck 64, is adapted to maintain the axis of the source 86 to the central axis 76 such that the radiation 101 can be aligned with the driving axis 62. The cannulated chuck 64 can either be made from materials with radiolucent properties or radiopaque properties. Instead of a chuck that requires a key to open and close, a quick-release chuck is possible. A quick-release chuck mates to features on a drill bit shank where torque can be transferred. Quick-release chucks are commonly known in the art.

Optionally, a standard medical drill 14 can be used in conjunction with an offset cannulated adapter 24 as shown in FIG. 2 to transmit x-ray radiation through a cannulated drill bit 26 as shown in FIG. 2. An offset cannulated adapter 24 is a device that takes x-ray radiation on one axis and input torque from another axis and combines them using a standard medical drill 14 to transmit x-ray radiation and torque for a cannulated drill bit 26. The cannulated adapter 24 is shown in FIGS. 1 and 2. The cannulated adapter 24 has an input shaft 32, a cannulated chuck 64 and a radiolucent passage 38 through the housing giving access to the rear of the chuck. The drill as shown in FIG. 1 is a standard medical drill 14 and a cannulated adapter 24 combined with the x-ray source 12 inside of an outer housing 34 to have the same function as the cannulated drill 68 as shown in FIG. 3. Opposite the adapter 24 and coaxial to the chuck 64 is a receiving aperture to receive and align the x-ray source 12. The chuck 64 and mounting 60 have a radiolucent passage 38 about the driven axis 76 that travels through the cannulated adapter 24. The chuck 64, aperture 18, and passage 66 are coaxial. The cannulated adapter 24 has an input shaft 32 that rotates about a driving axis 62 offset from the chuck 64. A standard medical drill 14 drives the input shaft 32 through the mechanism contained in the adapter 24, torque is transferred into the chuck 64. The housing 34 or attachment 42 maintains the spatial relationship of the adapter 24 to the drill 14. The attachment 42 also prevents rotation of the adapter 24 relative to the drill 14. The adapter 24, attachment 42, and mounting allow the user to project x-ray radiation along the same axis as a drill. By attaching a cannulated drill bit 26, the drill 14 and radiation are coaxial. The cannulated adapter 24 can be made from materials with radiolucent properties or radiopaque properties, but the capability of passing some x-ray radiation from the source is necessary. If the adapter 24 is made of mostly radiopaque materials, only a portion of x-ray radiation 100 as shown in FIGS. 1 and 5 is passed from the chuck 64. If the adapter is made of mostly radiolucent materials, a larger field of radiation 101 is transmitted, in addition to the smaller field of radiation 100.

A medical cannulated drill bit 26 is a drill bit that is built similar to the standard drill bit and includes a radiolucent passage 104 (as shown in FIG. 2) that can pass a portion of x-ray radiation 100 through a central axis 36 from one end to the other. The portion of x-ray radiation 100 is shown in FIGS. 1 and 5. The cannulated drill bit 26 has a shank portion 98, a tip 110, a fluted portion 112 extending from the tip towards the shank portion, and has a passage 104 about a central axis 36 that travels completely through from the shank portion 98 to the tip 110. The cannulated drill bit 26 is made from materials that can be sterilized and are suitable for medical use. Cannulated drill bits 26 are commonly known in the art. The passage 104 has radiolucent properties; it does not have to be a physical hole. As shown, the drill bit has a consistent overall diameter but many cannulated drills have a short fluted portion with the portion between the shank 98 and the tip 110 being a smooth shaft. The tip 110 is the leading edge for cutting into a material (a bone 70 seen in FIG. 4A in particular). The fluted portion 112 is a spiral that has been cut into the outside diameter from the tip 110 towards the shank portion 98 that is designed to transport loose material away from the tip 110 as it is drilling. The shank portion 98 is designed to be held by the chuck 64. As the chuck 64 rotates, the drill bit 26 rotates along its central axis. The shank 98 can either be a smooth outer diameter or have quick-release features. FIG. 6 shows the drill bit 26 and panel 82 without a bone or nail in-between to show an occluded region 48. The cannulated drill bit 26 can be made up of radiolucent portions 46 and radiopaque or radiodense 44 portions as shown in FIG. 6. Radiodense portions 44 cast a shadow for x-ray radiation 101 creating an occluded area 48. The occluded area 48 is where a portion of the radiation 101 is obscured by the drill bit 26. The radiolucent portions 46 can exist along the length to minimize the occluded area 48. As the length of the radiodense portion 44 increases, the occluded area 48 increases.

While a standard nail 72 may have transverse holes that are used for alignment, a fiducial marker 50, as shown in FIGS. 4A and 4B, can be either separately installed into the standard nail 72 before it is inserted into the bone 70 or be integral to the nail. The fiducial marker 50 can be integral to the nail for more precise alignment. The fiducial marker 50 has a different radiodensity than the nail 72 or the transverse hole 74. Typically the nail 72 is more radiodense than the transverse hole 74 or the bone 70, but does not have to be. For proper alignment, the transverse hole 74 needs to show up on a radiograph, provided the x-ray radiation is lined up with the transverse hole 74 as shown in FIGS. 4a and 4b. The fiducial marker 50 can be something as simple as a pin that is physically located coaxial to the transverse hole 74 as shown in FIGS. 4a and 4b or be made from a structure of a different shape. The fiducial marker 50 can be something that is suspended inside a material with different radiodense properties to cause a contrasting shape on the display 84. For example, if the fiducial marker 50 is an elongate pin that is suspended coaxially to the transverse hole, it would show up as a dot with a properly aligned drill bit as shown in FIG. 4a. If the drill bit 26 was misaligned, the fiducial marker would show up as a line as shown in FIG. 4b, the length shown on the display 84 thereof being directly related to the amount of misalignment. The fiducial marker 50 could take the form of two intersecting flat surfaces where the axis of intersection is central and coaxial to the transverse hole 74. An aligned drill would show a crosshair shape. Other shapes or features in the nail can have fiducial marker properties without the fiducial marker 50 being a separate piece. For example, radiolucent or radiodense features in the nail 72 can signal the user (as viewed on the display 84) as to the alignment of the drill bit 26. It is possible to use pins, grids, or tubes of various sizes or shapes to help the user dial in the alignment. The fiducial marker 50 can be integral to the transverse hole 74 and made such that when the drilled hole 116 as shown in FIGS. 1 and 5 meets the transverse hole 74, the drill bit 26 begins to displace or destroy the fiducial marker 50 and/or any supporting material around the fiducial marker. As is commonly known in the art, any material that might remain inside the body after surgery must be biocompatible.

Instead of a cannulated drill 68 or cannulated attachment 24, a drill guide could be implemented. The drill guide locates the axis of x-ray radiation to the drilling axis by a set distance. With the known distance in the guide matching a known distance between a fiducial marker in the nail 72 and the transverse hole 74, a standard drill bit can be attached to a drill driver 14. A hole 116 can be drilled by setting the guide to be offset from the transverse hole 74 by the same known distance. A drill guide gives the option of using a standard drill and drill bit. Alignment is accomplished by aligning the offset fiducial marker to the hole 116 being drilled.

In order to make the hole 116 coaxial to transverse hole 74, the x-ray source 12 is installed into the rear of the cannulated drill 68 or cannulated attachment 24 such that the central axis of the source 86 is coaxial with the central axis of passage 66. Next, a cannulated drill bit 26 is installed to the drill via the chuck 64. This arrangement makes the driving axes 62 of the drill source 86, and drill bit 36 coaxial. The assembly with a cannulated drill, as described, is shown in FIG. 3. The assembly with a standard drill and cannulated attachment is shown in FIGS. 1 and 2. The intramedullary nail 72 and bone 70 are then placed between the drill driver 14, cannulated drill 68, and the imager panel 82 as shown in FIG. 1. The source 12, imager 80, and display 84 are enabled, making a portion of the bone with the nail visible on the display 84 as shown in FIGS. 4a and 4b. If the drill bit 26 is properly aligned, the hole 74 and/or fiducial marker 50 is visible as in FIG. 4a. If the drill bit 26 is not coaxial with the hole 74, then the hole becomes visible as in FIG. 4b or not visible at all in the cases of severe misalignment. As the user begins drilling, the alignment can be monitored by watching the display 84. Corrections in the position and alignment of the drill bit 26 can be accomplished by manipulating the position or angle of the drill 14, 68. In the event a fiducial marker 50 is located inside the transverse hole, the rotating drill bit would break apart or displace the fiducial marker 50 as the drill bit penetrates the transverse hole 74.

In the event the chuck 64 is radiopaque (or is very radiodense), a portion of radiation 100 is all that passes through the radiolucent passage 104 of the drill bit. This results in an image that only shows the hole 74 when the drill bit is in sufficient proximity and alignment. In the event the chuck 64 is radiolucent (or has radiolucent properties), radiation 100 passes through the hole 104 in the drill (as shown in FIG. 1 as a portion of radiation 100) and around it 101. Radiation 100 spreads out away from the source 12 and allows the user to see a greater area on the display 84.

Drill bits 120 with radiopaque 122 and radiolucent 124 portions as shown in FIG. 10 can be used to reduce the occluded area 152 as shown in FIG. 8. Material with radiolucent properties is prone to rapid wear or breakage when used directly to drill into bone. The drill bit 120 with the radiolucent portion 124 along with a standard drill bit material used on the tip 126 can be used. Because even radiolucent materials may attenuate x-ray radiation to some extent, the drill bit 120 may have a center hole 128 to make the radiolucent portion 124 into a cannulated portion. The drill bit 120, as shown, shows where the radiopaque portion 122 has a smaller shank portion 130 that is pressed into the center hole 128. It is contemplated that the radiopaque portion 122 is connected to the radiolucent portion 124 through other means, such as a spline or metal fusing.

Alternatively, the location or modification of the x-ray source 12 is possible. As shown in FIG. 1, the generator 22 is a point, radiating outward therefrom. The point size of existing x-ray sources is small (0.5 mm to 1.0 mm) to generate a sharp image. Unlike optics, x-ray radiation does not use lenses to focus, so a small point source is necessary to generate a sharp image. It is possible to have a larger spot size (>3 mm). A larger spot size has the benefit of decreasing the occluded area 48 at the expense of image sharpness.

It is also possible to use multiple x-ray generators that are off axis as shown in FIGS. 7 and 9. By placing a small generator 140 away from the central axis 146 of the drill, the occluded area 138 is moved as shown in FIG. 8. By placing a multiple of generators 140, 142, 144 around the central axis 146 of the drill, it is possible to reduce or eliminate the occluded area by controlling the generators in sequence or in tandem. FIG. 9 shows a front view of the embodiment in FIG. 7. The multiple generators 140, 142, and 144 are placed around the central axis 146 at 120 degree increments, though other angular orientations are possible.

Further, a generator 140 can be moveable around the central axis 146 of the drill. This allows a similar result as the multiple generator embodiment, but with a single source.

When multiple generators 140, 142, 144 or a moving generator is used, the image as viewed by the user could be unintelligible because of overlap or movement. Utilizing a system to process the control, the sources, and generated images, improves the image as produced on the display 84. A control system as incorporated in the display 84 or imager 80 can enable individual generators and overlay individual images as received on the panel 82 to form a composite image. By using multiple or a moving source, the occluded area 138 can be reduced or eliminated. For example (FIG. 8), enabling the source 140 creates a first image where the image is shifted downwardly on the imager 80, creating occluded area 150. Enabling source 144 shifts the image upwardly, creating occluded area 154. The area between the two is occluded area 152. When the resulting image is processed, only occluded area 152 remains. By overlaying the two and processing the images, an image can be generated where the occluded area is significantly smaller.

An annular x-ray source can be implemented instead of multiple generators or a moving generator. The annular x-ray source would cover a similar area as the multiple generators 140, 142, and 144 but be a continuous ring of x-ray radiation instead of individual sources.

Figure 11:
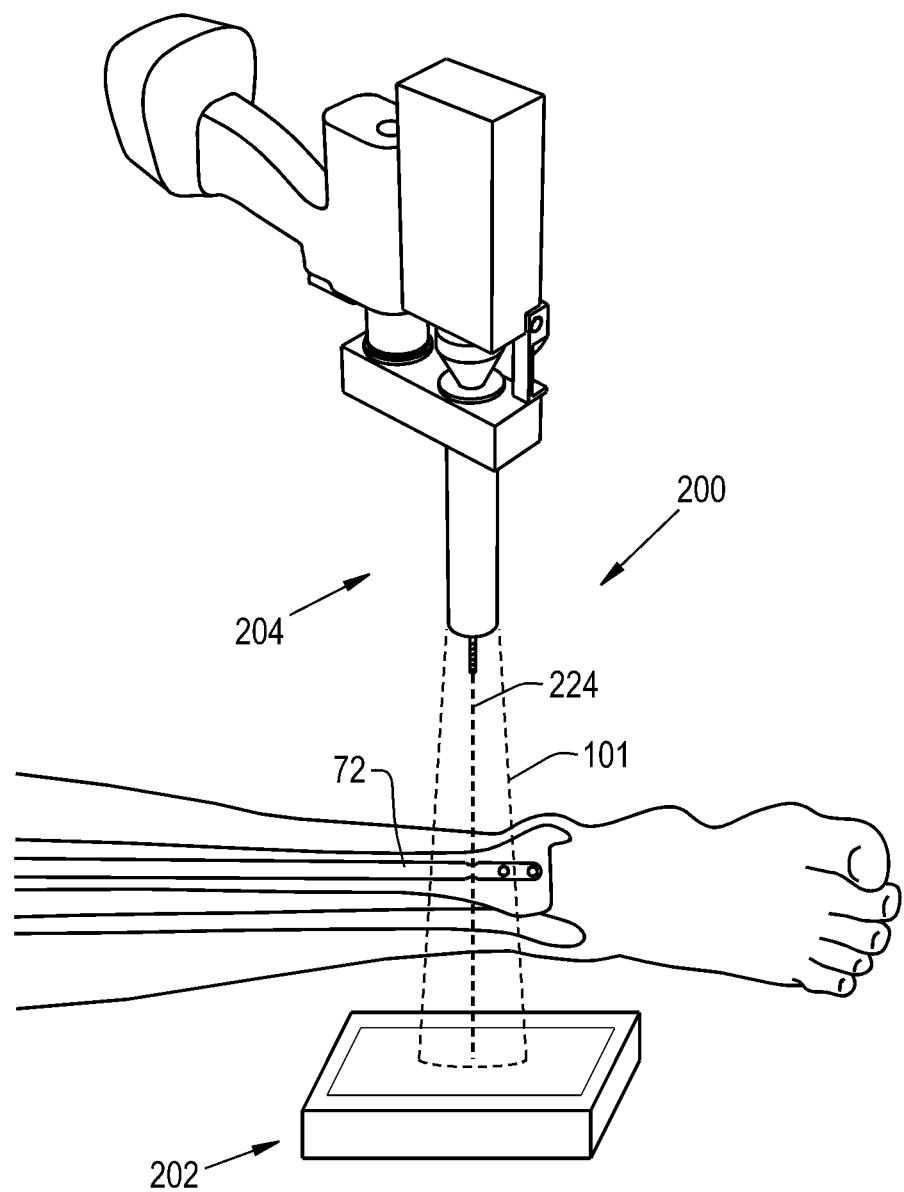
FIG. 11 illustrates an application of another embodiment of the present invention in the form of a surgical viewing system.
Figure 12:
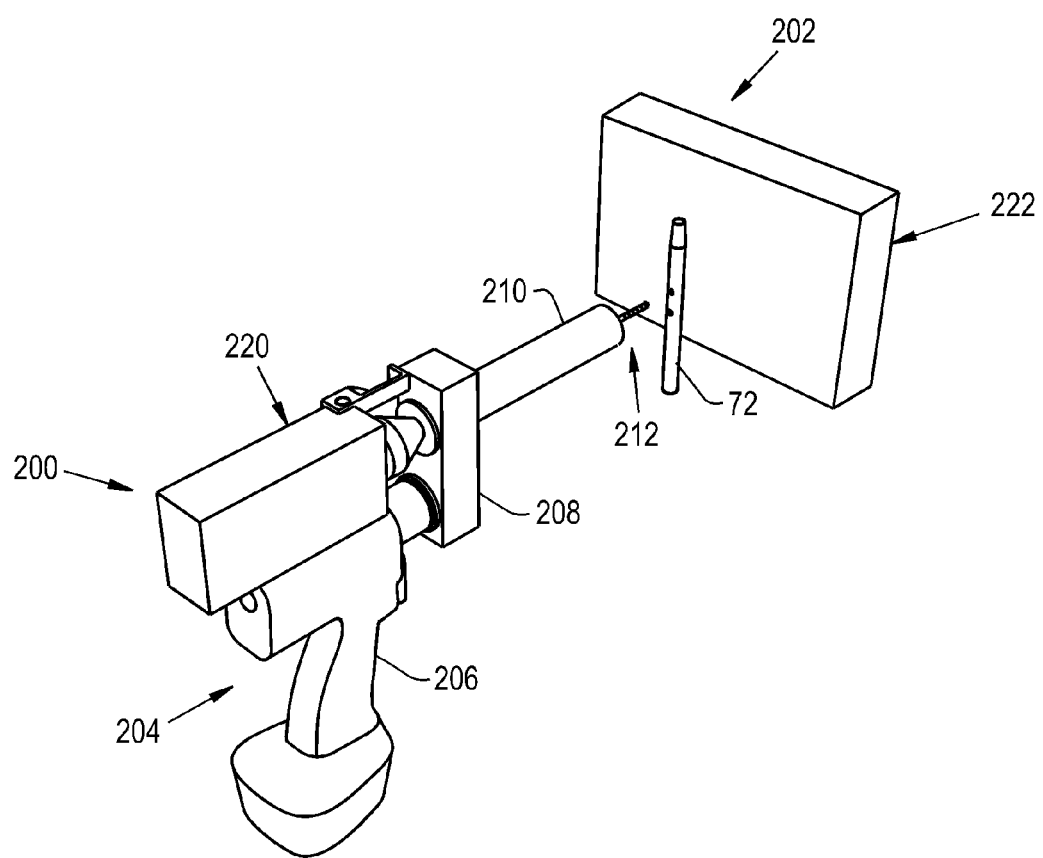
FIG. 12 is a perspective view of the viewing system of FIG. 11.

Now, additionally referring to FIGS. 11 and 12, there is shown another embodiment of the present invention in the form of a surgical system 200 having a viewing system 202 and a screw placing tool assembly 204. Surgical system 200 is shown relative to intramedullary nail 72. Tool assembly 204 includes a driver 206, an offset gear assembly 208, a chuck 210 and a bit assembly 212. Viewing system 202 includes an X-ray source 220, an X-ray detector 222, and a display 84 (not shown in FIG. 12 since the housing to which it is coupled is not shown). A beam of radiation 101 is emitted by source 220 about an axis 224, and an image is received by detector 222.

Figure 13:
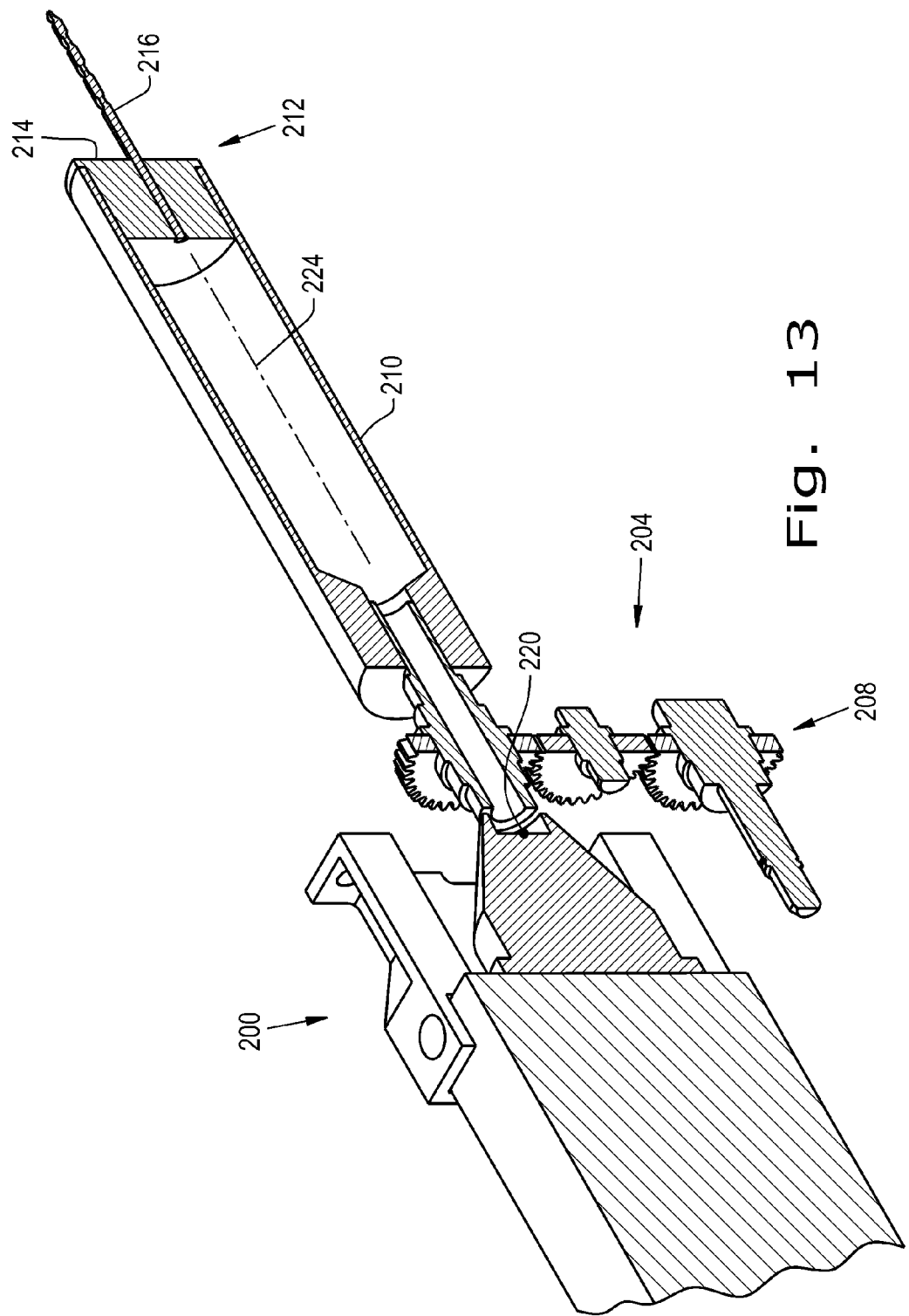
FIG. 13 illustrates in a schematical sectioned perspective view of a tool associated with the viewing system of FIGS. 11 and 12.
Figure 14:
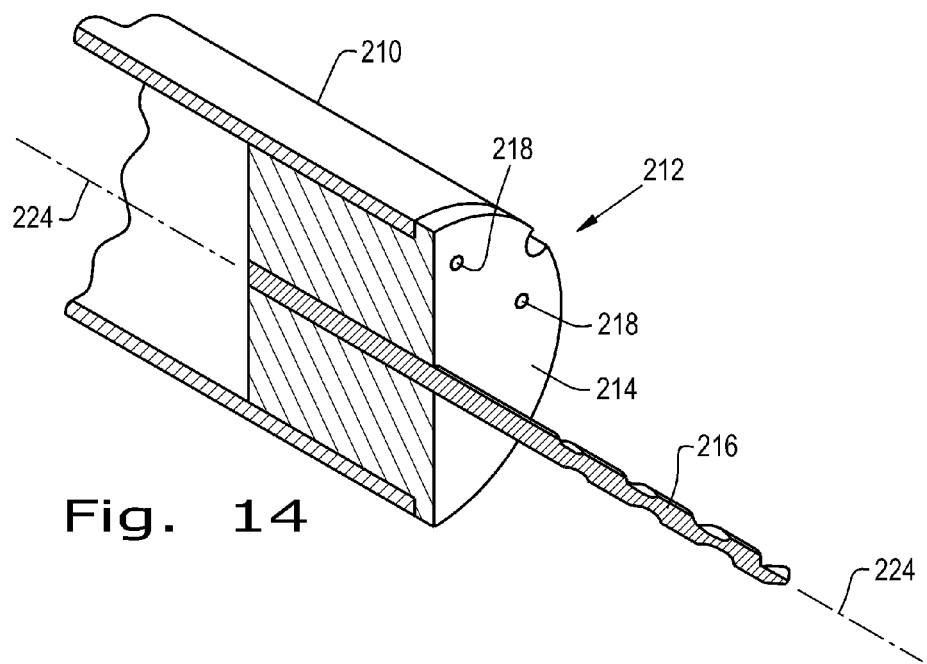
FIG. 14 is a perspective view of a part of the tool associated with the viewing system of FIGS. 11-13.

Additionally referring to FIGS. 13 and 14, bit assembly 212 includes a radiolucent shank 214, a drill bit 216 and fiducial markers 218. While a drill bit 216 is illustrated and is discussed as a bit herein, it can equally be a pedicle probe, awl or burr that is coupled to assembly 212 and guided by system 200. Fiducial markers 218 are positioned to provide a pattern, which may be situated in an axially symmetric formation, such as all being located the same or substantially the same distance from the rotational axis. Chuck 210 holds bit assembly 212 centered about axis 224. Gear assembly 208 rotates chuck 210 and hence bit assembly 212 about axis 224 when driven by driver 206. Radiation beam 101 travels through the hollow interior of chuck 210 as can be seen in FIG. 13 and the radiation passes through radiolucent shank 214, but the radiation that encounters fiducial markers 218 and drill bit 216 is reflected, deflected or absorbed.

Figure 15:
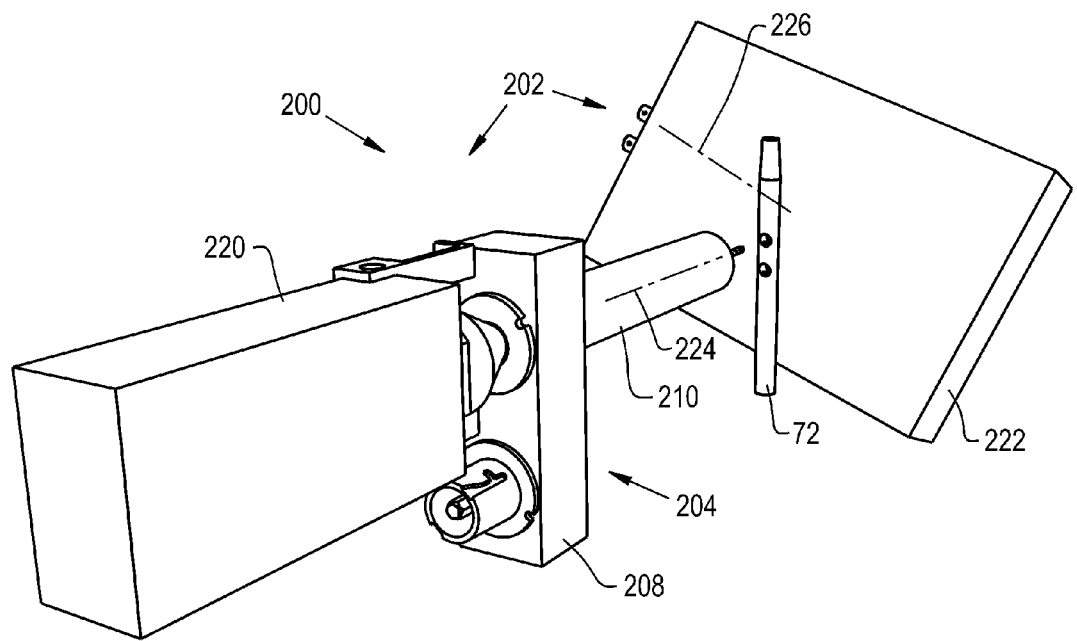
FIG. 15 is a perspective view of part of the viewing system showing part of the tool the X-ray source and the X-ray detector which is at a non-normal angle relative to the source.
Figure 16:
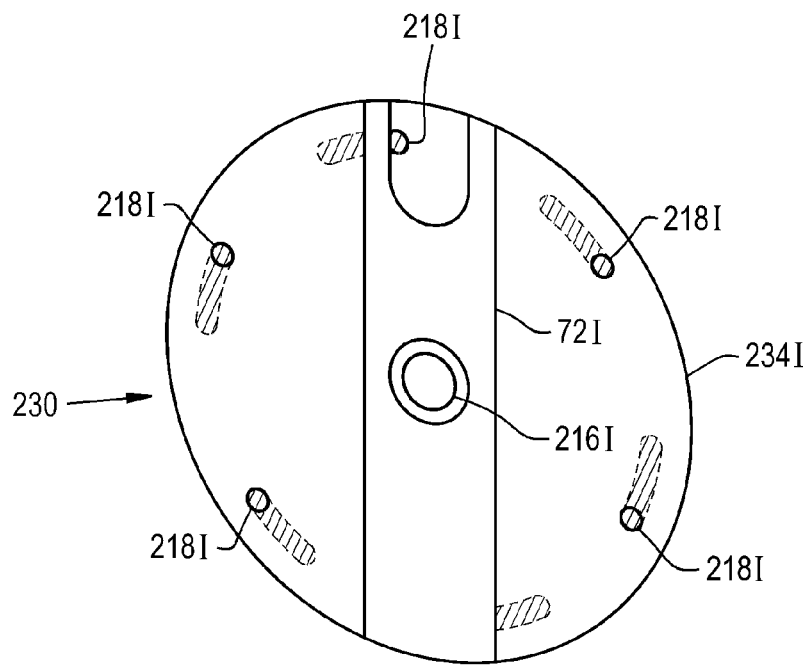
FIG. 16 illustrates an image as detected by the detector of FIG. 15.
Figure 17:
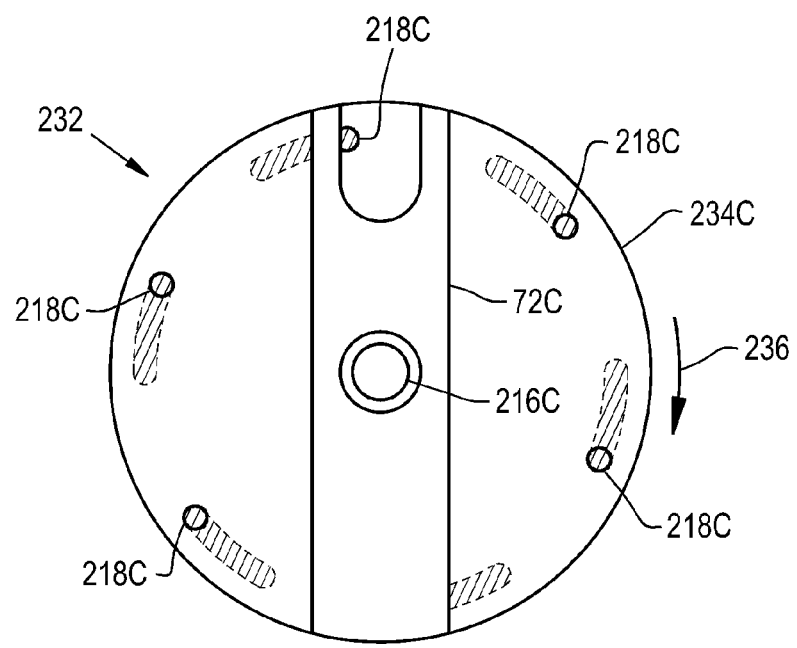
FIG. 17 illustrates the image as modified by the present invention for display on a display coupled to the tool associated with the viewing system of FIGS. 11-15.

Now, additionally referring to FIGS. 15-17 there is shown a realistic situation where detector 222 is not aligned normal to axis 224. Here detector 222 is shown skewed or angled relative to axis 224 with an axis 226 illustrating the misalignment. While the misalignment may be somewhat exaggerated to illustrate the functioning of the invention, the present invention advantageously removes the distortion caused by the misalignment so that the surgical procedure can successfully proceed. Image detector 222 receives an image 230 that is distorted and converts it into a corrected image 232, which is displayed on display 84.

Looking at image 230 the distortion or skewed image is detected by several elements of the image that are projected from the end of chuck 210/bit assembly 212. The "I" suffix to each element number indicates that it is the detected image of the reference number that precedes the "I". Here image 2161 is an oval, while the known shape of the cross-section of bit 216 is known to be circular. Additionally, the shape of images 2181 and their relative location and known geometrical positioning fiducial markers 218 also provide information to viewing system 202 to correct the image. Yet further, the overall footprint of radiation beam 101 coming from the circular end of chuck 210, which is the outer illuminated boundary 2341 of image 230 also provides information. Boundary 2341 is established, in this example, by the end of chuck 210, but it can be established by other elements of system 200, such as collimator 90. It should be noted that all of the discussed imaged elements are coupled to tool assembly 204. In contrast, the image 721 of intramedullary nail 72 cannot be relied upon to correct for distortion in the image, because intramedullary nail 72 may itself be misaligned, and the image of a feature of intramedullary nail 72 may be properly skewed because of such a misalignment.

Figure 18:
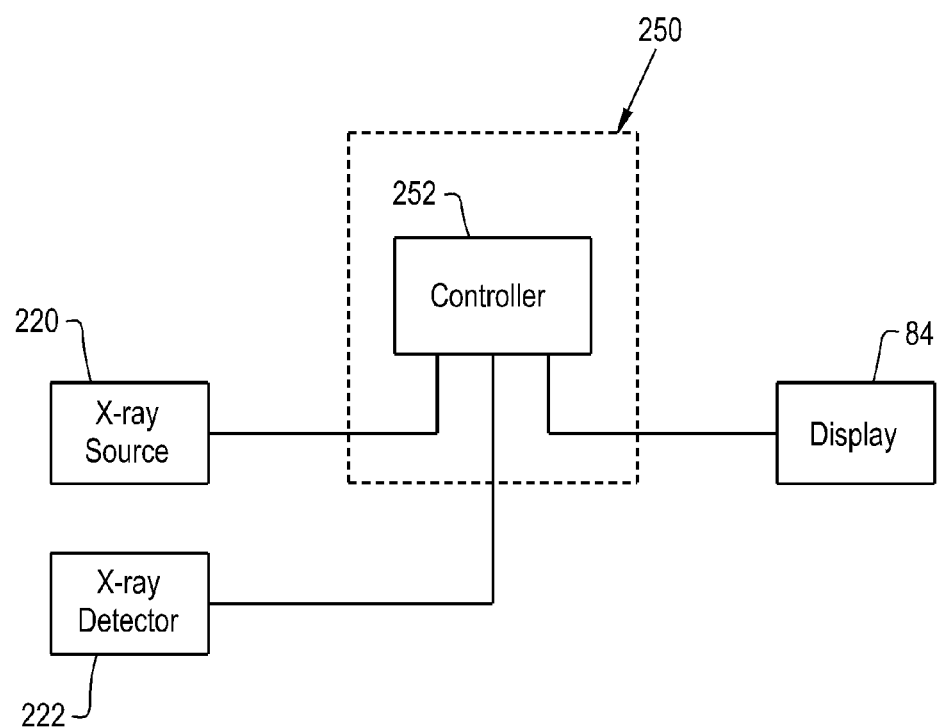
FIG. 18 schematically illustrates the aspects of an image processing unit that modifies a detected image to a corrected image for the viewing system of FIGS. 11-15.
Figure 19:
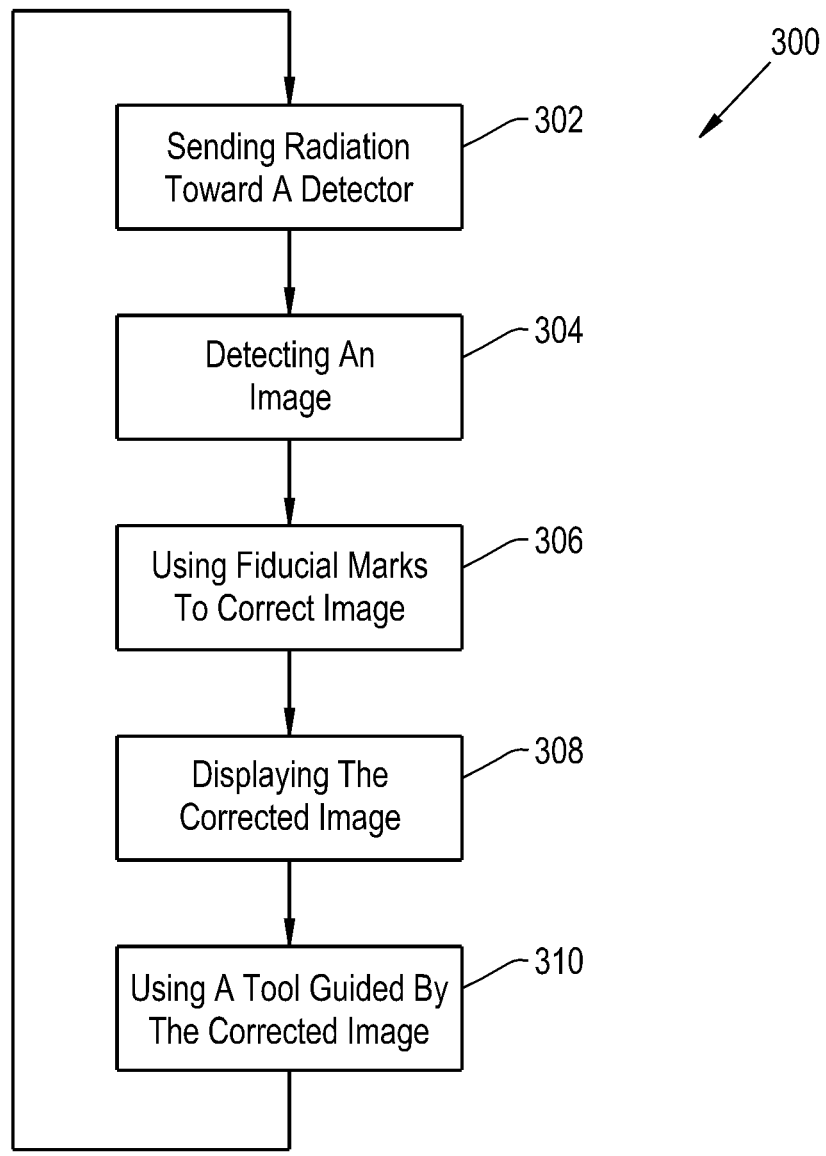
FIG. 19 illustrates, in a flowchart form, elements of a method used by the viewing system of FIGS. 11-15.

Additionally referring to FIGS. 18 and 19, viewing system 202 also includes an image correction system 250 that uses a controller 252 to operate a method 300 to alter detected image 230 into corrected image 232. In FIG. 17 the "C" suffix to each element number indicates that it is the corrected image of the reference number that precedes the "C". In image 232 the circular shapes of 216C and 218C are restored and the geometric location of images 218C is reestablished. Further the outer boundary of the image is returned to a circular shape. In the illustrated example the hole in intramedullary nail 72 is also circular in image 232, which only indicates that the hole in intramedullary nail 72 is substantially parallel with axis 224. Since image 216C shows that drill bit 216 is centered in the hole then the surgeon can proceed with the drilling operation to bore a hole through the bone where intramedullary nail 72 is located. If intramedullary nail 72 was misaligned relative to drill bit 216 then the shape of the hole in intramedullary nail 72 would be evident as well as any offset in drill bit 216 from the hole.

Controller 252 is coupled to display 84 and detector 222, and may be coupled to source 220. When source 220 is activated at step 302, controller 252 receives information from detector 222 in step 304. In step 306 fiducial marks are used to correct a received image 230 into corrected image 232. The corrected image 232 is then displayed on display 84 at step 308. The surgeon then uses tool 204, guided by corrected image 232 to move tool 204 and to carry out the surgical procedure, which is depicted herein as a drilling operation. Method 300 repeats itself so that the surgeon receives feedback as he/she manipulates tool 204.

Image correction system 250 has known geometric information on the position of fiducial markers 218 and boundary information of the end of chuck 210 that forms boundary 2341 and bit 216, so that the pixel information that is created is created into a plan view as if detector 222 were substantially or even perfectly normal to axis 224. Once the pixel information of the fiducial markers 218C are positioned where they should be in the corrected image then the intervening pixels are populated with data representative of the information in the pixels between the fiducial makers 2181. Techniques of interpolation and spatial mathematics are employed to create corrected image 232.

As bit 216 is rotated clockwise as indicated by arrow 236, tails appear on the marker images 2181, which can be displayed as marker images 218C in the corrected image 232. The shape of outer boundary 234 is used as a fiducial marker. In that as chuck 210 rotates the image is not blurred, and the line remains distinct, due to its axial symmetry about the axis of rotation 224. The elliptical shape in FIG. 16 of boundary 2341 is corrected in corrected image 232 and is shown as boundary 234C. In this way the correction algorithm can use the same data whether or not bit 216 is stationary or rotating.

It is also contemplated that image 232 can be kept approximately the same overall size as screw placing surgical tool 204 is moved toward or away from detector 222. This compensation takes into consideration that radiation beam 101 is somewhat conical in shape causing differing intersecting area of beam 101 to contact detector 222 as tool 204 is moved toward and away from detector 222.

To correct the perspective distortion present in this system 200, two aspects are included: (1) A fiducial marker of a known shape (in this embodiment, the inner opaque boundary of chuck 210) is fixed to the X-ray source 220 at a known location and orientation. The fiducial marker is positioned in front of the X-ray source 220, such that the marker image 2341 is projected onto the image plane when the X-ray source 220 is directed at the imager 222. (2) An image processor 250 with algorithm 300 and/or 400 is connected to the imager 222 and the display 84. The processor 250 receives the image from the imager 222, the algorithm 300, 400 performs a transformation on the image based on the information contained in the image 230, and the transformed image 232 is output to the display 84.

One aspect of the fiducial marker 234 is that it remains fixed with respect to the X-ray source axis 224. Thus, as the source 220 moves with respect to the imager 222 and the skew angle changes, the image of the fiducial 2341 in the radiograph is predictable and the skew angle can be deduced from the fiducial image 230.

Fiducial marker designs can be classified as to whether they are attached to the rotating chuck assembly 210 or not. Those that do not rotate with the chuck assembly have the advantage that their projected shape is not affected by the chuck's rotation. One example is a polygon-shaped collimator limiting the field of view, such as a square or hexagon. Another example is a set of points on the periphery of the field of view, such as individual spheres or notches in the collimator edge. From an image processing point of view, these examples are composed of straight lines and points.— Image elements composed of straight lines and points generally take fewer computational resources to identify and extract their position.

Fiducial markers that rotate with the chuck 210 have the advantage of being more easily integrated into the mechanical system. However, the chuck rotation can affect the appearance of the fiducial marker in the image. For example, fiducial markers that are polygon-shaped or a set of points may not appear the same when the chuck is rotating. Circular (or axially symmetric) fiducial markers will appear the same in the image regardless of whether the chuck is rotating. Circular designs have the disadvantage that they require a more resource-intensive algorithm to identify the curved boundary. Examples of suitable fiducial markers include the edge of a circular collimator, the edge of the chuck 210 and the edge of the drill bit 216. The drill bit 216 adds the disadvantage that it requires the bit or an equivalent shape to be present, so the system would not work when the bit is not in place.

It is also possible for the fiducial marker to be fixed to the imager instead of the X-ray source. However, this presents some limitations, notably that the X-ray source must illuminate the fiducial regardless of the position of the source. In addition, the fiducial must be placed some distance in front of the imager to provide the relief necessary to identify the perspective distortion. These requirements place additional restrictions on the design of the X-ray source and detector that limit the performance and utility of the system. All of which is overcome in the inventive solution of the present invention. The prior art does not disclose the placement of a screw through the hole of a nail or a plate located on or within a bone as discussed and claimed herein. Applicant's invention advantageously allows a surgeon to align a rotating tool and drill a hole and/or place a screw through a hole in nail 72.

Figure 20:
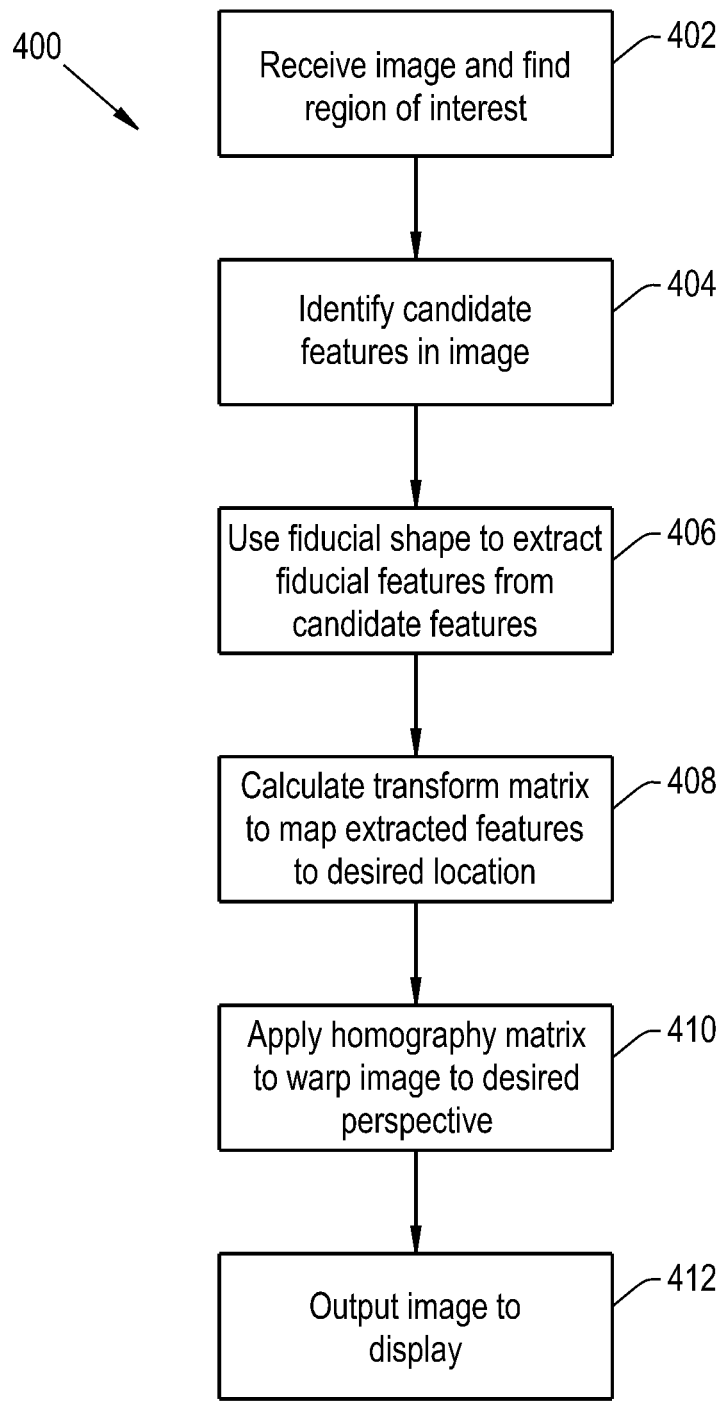
FIG. 20 illustrates, in a flowchart form, elements of a method to convert a detected image into a corrected image of the viewing system of FIGS. 11-15.

The algorithm 400 applies image-processing techniques to the image data to identify the position and shape of the fiducial mark in the image. The identified shape is compared to the ideal shape, and the parameters for a homographic transform are calculated. An outline of the algorithm is shown in FIG. 20.

Method 400 receives an image from the detector 222 and finds the region of interest, step 402, by thresholding for example. The region dimensions such as size, center, maximum and minimum intensity values are found for later use. Pixels outside the region of interest may be discarded to reduce the resources required for further processing.

Candidate features in the image are identified, at step 404, by using image processing algorithms, which can include edge, corner, line, circle and other detection techniques, or combinations of techniques.

At step 406, the expected size, shape and position of the fiducial marker in the image within the region of interest are used to extract the location of the fiducial features from the candidate features identified.

At step 408, a homography matrix is calculated using image-processing algorithms. Such algorithms find the optimal 3×3 orthogonal matrix that will map the fiducial features locations in the input image 230 to the desired location in the output image 232. At step 410, the homography matrix is applied to the input image, warping it to the desired perspective. The output image is sent to the display, at step 412.

One of the features of the present invention is the space between the X-ray source 220 and the shank of the drill bit (or tool) 216. Typically a spot size of the X-ray source 220 is less than 1 mm and a drill bit for a typical IM nail application is 4 mm or more in diameter, a significant distance between the spot 220 and the shank end of the bit 216 is necessary to be able to image the hole, which may typically be 5 mm, without the hole being occluded by the drill bit. In the inventive solution of the present invention at least 150 mm exists between X-ray source 220 and the shank of bit 216, preferably more than approximately 200 mm, or approximately around 200 mm is most preferable.

Prior art X-ray systems, whether diagnostic or interventional (surgical), flood the detector with radiation. Prior art sources teach that the detector should be flooded and the field of illumination should be wide, say 45 degrees. However, the present invention uses an application of X-rays that is narrow and limited, because the tool is used at a point in the procedure where the only important information is the target axis and closely surrounding tissue, so the present invention advantageously eliminates unnecessary radiation. Another advantage of the present invention is the reduction in the use of radiolucent materials that is possible since a narrow field of illumination is used, to thereby reduce the wide spread use of radiolucent materials that are required to have a wide field of illumination. Typically radiolucent materials are not as durable as conventional materials and they do not hold up well to autoclave cycles, so eliminating them improves reliability of the overall system. Furthermore, the narrow field of illumination allows the present invention to use the edge of the field as the fiducial marker. Advantageously the present invention depends on not flooding the detector so that the edge of the field of illumination is contained in the detected image. To avoid unnecessary exposure, the present invention has limited the field of illumination to a minimum practical size. In a current embodiment of the invention, the hardware surrounding the X-ray source axis is radiopaque to limit the radiation exiting the tool to a narrow cone. Hardware components including the bearings and gears surrounding the chuck, the chuck itself, and the offset drive housing block the radiation. In one embodiment of the present invention the field of view is limited to a solid angle of about 8 degrees and a diameter of about 25 mm at the end of the tool, but the optimal field of illumination will vary with the needs of the specific application. Generally, a field of view of up to 50 mm in diameter and a solid angle of up to 20 degrees will work for screw placement. This is substantially less than what the prior art suggests.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical viewing system, comprising:
   an X-ray source creating a beam of radiation;
   a handheld screw placing surgical tool with the X-ray source connected thereto, the screw placing surgical tool having an axis of rotation;
   an X-ray detector positioned to detect a projected image resulting in a detected image, the detected image resulting from receiving at least some of the beam of radiation by the detector;
   at least one fiducial marker coupled to a part of the handheld screw placing surgical tool, the at least one fiducial marker being radiopaque and blocking a portion of the beam of radiation from the detector to produce a profile on the detected image; and
   an image correction system taking the detected image and producing a corrected image by using at least one of a shape of the profile of the fiducial marker and a location of the profile of the fiducial marker.

2. The viewing system of claim 1, wherein the fiducial marker is axially symmetric to the axis of rotation.

3. The viewing system of claim 1, wherein the detector is at a non-normal angle relative to the beam of radiation.

4. The viewing system of claim 3, wherein the screw placing surgical tool includes a radiopaque tool portion that is configured to enter an animal body to perform a function therein, the radiopaque tool portion serving as a marker, the image correction system also using a projection of the radiopaque tool portion on the detected image to produce the corrected image.

5. The viewing system of claim 4, wherein the radiopaque tool portion is a drill bit.

6. The viewing system of claim 1, wherein the at least one fiducial marker includes a plurality of fiducial markers arranged in a geometrical pattern.

7. The viewing system of claim 6, wherein the fiducial markers are arranged in a plane that is substantially perpendicular to the beam of radiation.

8. The viewing system of claim 6, wherein the relative locations of the fiducial markers is used by the image correction system to produce the corrected image from the detected image.

9. The viewing system of claim 1, wherein the screw placing surgical tool further includes a radiolucent shank that holds one of a drill bit, a pedicle probe, an awl and a burr.

10. The viewing system of claim 9, wherein the at least one fiducial marker is a plurality of fiducial markers that are embedded in the radiolucent shank radially outward from the drill bit, the pedicle probe, the awl or the burr.

11. A method of viewing a surgical item in an animal, the method comprising the steps of:
    creating a beam of radiation from an X-ray source that is connected to a screw placing surgical tool, the screw placing surgical tool having an axis of rotation, the beam of radiation being generally centered about the axis of rotation;
    detecting a projected image with an X-ray detector resulting in a detected image, the detected image resulting from receiving at least some of the beam of radiation by the detector;
    coupling at least one fiducial marker to a part of the screw placing surgical tool, the at least one fiducial marker being radiopaque and blocking a portion of the beam of radiation from reaching the detector to produce a profile on the detected image, the fiducial marker being axially symmetric to the axis of rotation; and
    correcting the detected image and producing a corrected image with an image correction system using at least one of a shape of the profile of the fiducial marker and a location of the profile of the fiducial marker.

12. The method of claim 11, further comprising the step of displaying the corrected image on a display coupled to the screw placing surgical tool.

13. The method of claim 11, wherein the detector is at a non-normal angle relative to the beam of radiation.

14. The method of claim 13, wherein the screw placing surgical tool includes a radiopaque tool portion that is configured to enter the animal to perform a function therein, the radiopaque tool portion serving as a marker, the image correction system also using a projection of the radiopaque tool portion on the detected image to produce the corrected image.

15. The method of claim 14, wherein the radiopaque tool portion is a drill bit.

16. The method of claim 11, wherein the at least one fiducial marker is a plurality of fiducial markers arranged in a geometrical pattern.

17. The method of claim 16, wherein the fiducial markers are arranged in a plane that is substantially perpendicular to the beam of radiation.

18. The method of claim 16, wherein the relative locations of the fiducial markers is used by the image correction system to produce the corrected image from the detected image.

19. The method of claim 16, wherein the screw placing surgical tool further includes a radiolucent shank that holds one of a drill bit, a pedicle probe, an awl and a burr.

20. The method of claim 19, wherein the fiducial markers are embedded in the radiolucent shank radially outward from the drill bit, the pedicle probe, the awl or the burr.

* * * * *

UNITED STATES PATENT AND TRADEMARK OFFICE
CERTIFICATE OF CORRECTION

PATENT NO. : 9,782,183 B1
APPLICATION NO. : 15/445215
DATED : October 10, 2017
INVENTOR(S) : David B. Rich It is certified that error appears in the above-identified patent and that said Letters Patent is hereby corrected as shown below:

In the Specification

Column 9
At Line 64, please delete "2161", and substitute therefore --216I--; and
At Line 66, please delete "2181", and substitute therefore --218I--.

Column 10
At Line 4, please delete "2341", and substitute therefore --234I--;
At Line 5, please delete "2341", and substitute therefore --234I--;
At Line 9, please delete "721", and substitute therefore --72I--;
At Line 48, please delete "2341", and substitute therefore --234I--;
At Line 55, please delete "2181", and substitute therefore --218I--;
At Line 58, please delete "2181", and substitute therefore --218I--; and
At Line 64, please delete "2341", and substitute therefore --234I--.

Column 11
At Line 14, please delete "2341", and substitute therefore --234I--.

Signed and Sealed this
Twenty-sixth Day of June, 2018

Andrei Iancu
*Director of the United States Patent and Trademark Office*